United States Patent [19]

Darragh et al.

[11] 4,125,562
[45] Nov. 14, 1978

[54] PREPARATION OF 4,4'-DIHYDROXYDIPHENYLSULFONES

[75] Inventors: John I. Darragh, Runcorn; John B. Rose, Letchworth, both of England

[73] Assignee: Imperial Chemical Industries Limited, London, England

[21] Appl. No.: 877,735

[22] Filed: Feb. 14, 1978

[30] Foreign Application Priority Data

Feb. 18, 1977 [GB] United Kingdom ............... 6900/77

[51] Int. Cl.$^2$ .......................................... C07C 147/10
[52] U.S. Cl. ............................................. 260/607 AR
[58] Field of Search ................................ 260/607 AR

[56] References Cited

U.S. PATENT DOCUMENTS 2,000,061  5/1935  Carr ............................... 260/607 AR

FOREIGN PATENT DOCUMENTS 165,526  2/1953  Australia ......................... 260/607 AR
106,936  8/1975  Japan .............................. 260/607 AR Primary Examiner—Lewis Gotts
Assistant Examiner—Molly C. Eakin
Attorney, Agent, or Firm—Cushman, Darby & Cushman

[57] ABSTRACT

A phenol is reacted with sulphur trioxide in the presence of liquid hydrogen fluoride to form a 4,4'-dihydroxydiphenylsulphone. A molar excess of hydrogen fluoride and stoichiometric proportions of sulphur trioxide and phenol or a slight excess of sulphur trioxide over phenol are preferred.

9 Claims, No Drawings

PREPARATION OF 4,4'-DIHYDROXYDIPHENYLSULFONES

This invention relates to organic sulphur compounds, in particular to diphenylsulphones, and especially to 4,4'-dihydroxydiphenylsulphones.

4,4'-dihydroxydiphenylsulphone:

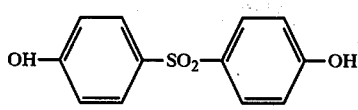

is conventionally manufactured by the reaction of phenol with oleum. The product obtained from this reaction generally contains large amounts of a variety of different impurities and is frequently highly coloured. Thus extensive purification may be required before an acceptable final product is obtained.

According to the present invention there is provided a process for the manufacture of a 4,4'-dihydroxydiphenylsulphone which comprises reacting a phenol with sulphur trioxide in the presence of liquid hydrogen fluoride.

The process of the present invention is especially suitable for the manufacture of unsubstituted 4,4'-dihydroxydiphenylsulphone from unsubstituted phenol, but the term "a 4,4'-dihydroxydiphenylsulphone" as used herein includes a substituted 4,4'-dihydroxydiphenylsulphone and the term "a phenol" includes a correspondingly substituted phenol, being unsubstituted in the 4-position. Suitable substituents are those which favour substitution in the 4-position. Thus examples of suitable starting materials include ortho-cresol and ortho-chlorophenol.

The primary product of the process of the present invention is a 4,4'-dihydroxydiphenylsulphone. A minor proportion of the corresponding 2,4'-dihydroxydiphenylsulphone may also be produced during the course of the reaction and may if desired be separated from the reaction mixture and recovered as co-product. In general, however the 2,4'-dihydroxydiphenylsulphone is not required as a co-product and it is desirable to minimise its formation in the reaction as hereinafter described.

The process of the present invention may be a batch process or a continuous process.

It is to be understood that sulphur trioxide forms an adduct with liquid hydrogen fluoride and may be present in the form of this adduct—fluoro-sulphonic acid (HFSO$_3$). The sulphur trioxide may be added to the reaction mixture either as such or in the form of the fluorosulphonic acid adduct.

The ratio of phenol to sulphur trioxide is preferably in the range from 0.2 to 5 moles of phenol per mole of sulphur trioxide. Substantially stoichiometric proportions or a slight excess of sulphur trioxide (for example from 1 to 2 moles of phenol per mole of sulphur trioxide) is especially preferred.

The liquid hydrogen fluoride used in the reaction is preferably substantially free of water. However, precautions rigidly to exclude water are not generally necessary and indeed 1 mole of water is produced per mole of product during the reaction. We have found that the presence in the hydrogen fluoride used in the reaction of up to about 1 mole of water per 2 moles of phenol (i.e. a proportion after reaction of 2 moles of water per mole of product) does not significantly affect the course of the reaction.

The hydrogen fluoride is preferably present in molar excess relative to the sulphur trioxide. A ratio of hydrogen fluoride to sulphur trioxide in excess of 10 moles hydrogen fluoride per mole of sulphur trioxide is especially preferred. There is no particular upper limit to the amount of hydrogen fluoride which may be used, but little advantage is to be gained in using a proportion of hydrogen fluoride of greater than 50 moles hydrogen fluoride per mole of sulphur trioxide.

The reaction temperature is preferably below 200° C., since char formation and undesirable product discolouration may take place at higher temperatures. Thus a reaction temperature of from 20° C. to 160° C., for example 20° C. to 150° C., is especially suitable. We have found that the proportion of the 2,4'-dihydroxydiphenylsulphone in the product depends on the reaction temperature employed, the proportion of the 2,4'-dihydroxydiphenylsulphone being reduced at relatively higher temperatures. Thus if it is desired to minimise the proportion of the 2,4'-dihydroxydiphenylsulphone in the production, a reaction temperature of from 100° C. to 160° C. is preferred. A reaction temperature of about 130° C. is especially suitable.

Typical reaction times range from 5 minutes to 24 hours depending inter alia on the reaction temperature. Residence times for a continuous reaction may be determined by simple trial.

The reaction conveniently takes place under autogenous pressure, although external pressure may be applied if desired. Typical pressures range from 40 psig to 350 psig.

The desired product may be separated from the reaction mixture by conventional techniques, including for example solvent extraction.

4,4'-dihydroxydiphenylsulphone is useful as a polymer precursor, in tanning and leather industries and in electroplating.

If the 4,4'-dihydroxydiphenylsulphone is required for use as a polymer precursor, a product which, after purification, is colourless or has a minimum of colouration is highly desirable. It is an advantage of the process of the present invention that a relatively colourless product may be obtained after a conventional product recovery and purification stage.

The invention is illustrated by the following Examples.

EXAMPLE 1

A 500 ml autoclave was charged with 14 gms of fluorosulphonic acid (HFSO$_3$) and 20 gms phenol. The autoclave was cooled to $-100°$ C. and 150 gms of anhydrous hydrogen fluoride were added. The autoclave was allowed to warm to room temperature with stirring and was then heated at 75° C. for 6 hours giving an autogenous pressure of 85 psig.

The autoclave was cooled to 0° C. and the volatile material was vented off. The remaining contents of the autoclave were poured into crushed ice and precipitated a pale buff-coloured solid which was filtered and washed with water. On drying, 24 gms of product containing 87.6% by weight of 4,4'-dihydroxydiphenylsulphone and 12.4% by weight of 2,4'-dihydroxydiphenylsulphone (essentially no other impurities being detectable by gas-liquid chromatography) was isolated.

This product was purified by solvent extraction to recover the desired 4,4'-dihydroxydiphenylsulphone and the purified product thus obtained was colourless.

EXAMPLE 2

The procedure of Example 1 was repeated except that the autoclave was heated at 130° C. for 6 hours. 23 gms (wet) of a dark brown solid were isolated which on analysis by infra-red spectroscopy, nuclear magnetic resonance spectroscopy and mass spectroscopy showed a similar product composition to that of Example 1 together with additional impurities consistent with $C_6H_5SO_3F$ and $C_{18}H_{14}SO_3$.

EXAMPLE 3

The procedure of Example 1 was repeated except that 80 gms of phenol were reacted with 56 gms of fluorosulphonic acid in 300 gms of hydrogen fluoride. The autoclave was heated at 75° C. for 12 hours. 112 gms of a pale buff-coloured solid were isolated. Analysis showed the composition of the product to be essentially similar to that of Example 1.

EXAMPLES 4 TO 13

The procedure of Example 1 was repeated using the proportions of reactants given in Table I. The crude product from the autoclave contained essentially only 4,4'-dihydroxydiphenylsulphone and 2,4'-dihydroxydiphenylsulphone (traces only of other compounds being detected by nuclear magnetic resonance spectroscopy, mass spectroscopy and gas/liquid chromatography).

The percentage by weight of 2,4'-dihydroxydiphenylsulphone in the crude product (Table I) was determined by gas/liquid chromatography. The combined yield of 2,4'- and 4,4'-dihydroxydiphenylsulphone was approaching stoichiometric in each case.

The buff-coloured crude product from the autoclave in Examples 6 to 15 was treated with charcoal and recrystallised from water. In each case a colourless solid was obtained with a 2,4'-dihydroxydiphenylsulphone content of less than 1% by weight. For example, the product from Example 7, purified as above, gave colourless crystals containing 99.3% by weight of 4,4'-dihydroxydiphenylsulphone and 0.7% 2,4'-diphenylsulphone.

TABLE 1

| Ex. | Reaction Temperature | Reaction Time (Hrs) | Weight Of Reactants (g) | | | Molar Ratio Of Reactants | | | 2,4'-Dihydroxy-diphenyl Sulphone In Crude Product | Colour Of Crude Product |
|---|---|---|---|---|---|---|---|---|---|---|
| | | | Phenyl | HFSO$_3$ | HF | Phenol | Sulphur Trioxide | Hydrogen Fluoride | | |
| 4 | 75 | 6 | 20 | 10.4 | 150 | 2 | 1 | 70 | 20 | Buff |
| 5 | 75 | 12 | 80 | 56 | 150 | 2 | 1 | 35 | 18 | Buff |
| 6 | 130 | 1 | 20 | 14 | 150 | 2 | 1.5 | 70 | 3.0 | Buff |
| 7 | 130 | 1 | 30 | 21 | 150 | 2 | 1.5 | 46 | 4.1 | Buff |
| 8 | 130 | 1 | 40 | 28 | 150 | 2 | 1.5 | 35 | 3.5 | Brown |
| 9 | 130 | 1 | 60 | 42 | 150 | 2 | 1.5 | 23 | 3.6 | Buff |
| 10 | 145 | 1 | 20 | 14 | 150 | 2 | 1.5 | 70 | 3.6 | Buff |
| 11 | 160 | 1 | 20 | 14 | 150 | 2 | 1.5 | 70 | 2.3 | Dark Brown |
| 12 | 130 | 10mins | 20 | 14 | 150 | 2 | 1.5 | 70 | 3.3 | Pale Buff |
| 13 | 130 | 1 | 20 | 10.4 | 150 | 2 | 1 | 70 | 3.3 | Buff |

What we claim is:

1. A process for the manufacture of a 4,4'-dihydroxydiphenylsulphone which comprises reacting a phenol with sulphur trioxide in the presence of liquid hydrogen fluoride.

2. A process according to claim 1 wherein the ratio of phenol to sulphur trioxide is from 0.2 to 5 moles of phenol per mole of sulphur trioxide.

3. A process according to claim 2 wherein the ratio of phenol to sulphur trioxide is from 1 to 2 moles of phenol per mole of sulphur trioxide.

4. A process according to claim 1 wherein the ratio of hydrogen fluoride to sulphur trioxide is greater than 10 moles of hydrogen fluoride per mole of sulphur trioxide.

5. A process according to claim 1 wherein the reaction temperature is not greater than 200° C.

6. A process according to claim 1 wherein the reaction temperature is from 20° C. to 160° C.

7. A process according to claim 1 wherein the reaction temperature is from 100° C. to 160° C.

8. A process according to claim 1 wherein the reaction temperature is from 20° C. to 150° C.

9. A process according to any one of the preceding claims wherein the phenol is unsubstituted phenol and the corresponding product is unsubstituted 4,4'-dihydroxydiphenyl sulphone.

* * * * *